US010285934B1

(12) United States Patent
Sharma et al.

(10) Patent No.: US 10,285,934 B1
(45) Date of Patent: May 14, 2019

(54) ADMINISTRATION OF A DRUG THROUGH THE BLOOD BRAIN BARRIER USING STIMULI-RESPONSIVE NANOPARTICLES

(71) Applicant: Battelle Memorial Institute, Columbus, OH (US)

(72) Inventors: Gaurav Sharma, Lewis Center, OH (US); Chad Bouton, Powell, OH (US)

(73) Assignee: Battelle Memorial Institute, Columbus, OH (US)

( * ) Notice: Subject to any disclaimer, the term of this patent is extended or adjusted under 35 U.S.C. 154(b) by 7 days.

(21) Appl. No.: 15/340,923

(22) Filed: Nov. 1, 2016

Related U.S. Application Data

(60) Provisional application No. 62/249,344, filed on Nov. 1, 2015.

(51) Int. Cl.
*A61K 9/00* (2006.01)
*A61K 47/02* (2006.01)
*A61N 1/32* (2006.01)
*A61N 2/00* (2006.01)
*A61N 2/02* (2006.01)

(52) U.S. Cl.
CPC .......... *A61K 9/0009* (2013.01); *A61K 9/0085* (2013.01); *A61K 47/02* (2013.01); *A61N 1/327* (2013.01); *A61N 2/004* (2013.01); *A61N 2/02* (2013.01)

(58) Field of Classification Search
CPC .... A61K 9/0009; A61K 9/0085; A61K 47/02; A61N 1/327; A61N 2/02; A61N 2/004
See application file for complete search history.

(56) References Cited

U.S. PATENT DOCUMENTS

| 4,813,399 | A | 3/1989 | Gordon |
| 8,968,699 | B2 | 3/2015 | Jin et al. |
| 9,636,517 | B2 | 5/2017 | Pell |
| 9,724,503 | B2 | 8/2017 | Khizroev et al. |
| 2011/0044911 | A1 | 2/2011 | Aktari et al. |
| 2011/0213193 | A1 | 9/2011 | Nair et al. |
| 2013/0317279 | A1* | 11/2013 | Khizroev ............... A61N 2/006 600/12 |
| 2013/0338039 | A1* | 12/2013 | Mazed ............... G01N 21/6454 506/16 |
| 2014/0227186 | A1 | 8/2014 | Rademacher |
| 2015/0126964 | A1 | 5/2015 | Martel |
| 2016/0346389 | A1 | 12/2016 | Friedman et al. |

FOREIGN PATENT DOCUMENTS

| WO | WO 2013170379 A1 * | 11/2013 | ........... A61K 31/704 |
| WO | WO-2013170379 A1 * | 11/2013 | ........... A61K 31/704 |

OTHER PUBLICATIONS

Nair, M. et al., Externally controlled on-demand release of anti-HIV drug using magneto-electric nanoparticles as carriers, Apr. 16, 2013, Nature Communications, Macmillan Publishers Ltd.,4:1707.*
Kong, Seong, Deok et al., "Magnetic targeting of nanoparticles across the intact blood-brain barrier", Journal of Controlled Release 164 (2012) pp. 49-57.
Tabatabaei, S.J. , et al. "Remote control of the permeability of the blood-brain barrier by magnetic heating of nanoparticles: A proof of concept for brain drug delivery", Journal of Controlled Release, 206 (2015) p. 49-57.
Thomsen LB, et al., "Uptake and Transport of Superparamagnetic Iron Oxide Nanoparticles through Human Brain capillary Endothelial Cells", ACS Chem. Neurosci. Oct. 16, 2013; 4(10), pp. 1352-1360.

* cited by examiner

*Primary Examiner* — Amber R Stiles
(74) *Attorney, Agent, or Firm* — Frank Rosenberg; C. Michael Gegenheimer

(57) ABSTRACT

A method of administering a drug into the brain of a mammal (human or nonhuman) is described. In this method, a magneto-electric nanoparticle (MENP) and a drug are injected into the blood stream of a mammal. The MENP attaches to the blood-brain barrier (BBB) and a non-alternating electric or magnetic field is applied. In an alternative, the non-alternating field could be replaced by a slowly alternating field so as to avoid localized heating. The step of applying an electric or magnetic field causes an increase in the permeability of the BBB to the drug so that the drug passes into the brain while the MENP remains attached to the BBB.

18 Claims, No Drawings

ADMINISTRATION OF A DRUG THROUGH THE BLOOD BRAIN BARRIER USING STIMULI-RESPONSIVE NANOPARTICLES

RELATED APPLICATIONS

This application claims the priority benefit of U.S. Provisional Patent Application Ser. No. 62/249,344 filed Nov. 1, 2015.

BACKGROUND OF THE INVENTION

There have been great efforts devoted to improving methods for safely transporting drugs across the blood brain barrier (BBB). Recently, a large amount of research has been directed to the application of electric or magnetic fields to facilitate the transport of drugs across the BBB.

Martel et al. in US 2015/0126964 state that magnetically heatable entities (MHEs) can be piloted from an injection point to a location of the BBB and then using an alternating magnetic field to heat the MHEs. Advantageously the MHEs are superparamagnetic. Application of an AC field heats the MHEs leading to transient disruption of the BBB, thus facilitating delivery of therapeutic agents. A scientific paper by several of the inventors of the Martel patent application is Tabatabaei S J, Girouard H, Carret A-S, Martel S., entitled "Remote control of the permeability of the blood-brain barrier by magnetic heating of nanoparticles: A proof of concept for brain drug delivery", Journal of Controlled Release, 206 (2015) page 49-57. The authors reported that "we show that the thermal energy generated by magnetic heating (hyperthermia) of commercially available magnetic nanoparticles (MNPs) in the brain capillaries of rats can transiently increase barrier permeability . . . . Results indicate a substantial but reversible opening of the BBB where hyperthermia is applied." In this paper, the authors stated that "when MNPs are deposited, they remain on the surface of the target endothelium for the duration of our technique."

Several patents have discussed nanoparticles and the BBB. International patent application no. WO201474584 describes a method comprising administering to a subject a plurality of magneto-electric nanoparticles (MENP) having a drug associated thereto through an ionic bond; and applying a magnetic field to the subject to weaken the ionic bond thereby releasing at least a portion of the drug from the MENP. The MENP may be $CoFe_2O_4$@$BaTiO_3$. Khizroev et al. in US 20130317279 describe a method of using magneto-electro nanoparticles that pass through the BBB into the brain where they are actuated by an external AC magnetic field. Jin et al. in U.S. Pat. No. 8,968,699 describe hollow nanospheres comprising a drug (such as an anti-nerve agent) and further comprising magnetically actuable superparamagnetic nanoparticles and a polymer coating. A magnetic field can be used to activate the nanospheres and release drug inside the brain. The nanoparticles can be heated to disrupt the BBB for easier crossing.

WO2014125256 describes a method of delivering at least one agent to the central nervous system (CNS). The composition comprises: (a) a nanoparticle comprising: (i) a magnetic core; (ii) a corona comprising a plurality of ligands covalently linked to the core, wherein said ligands comprise a carbohydrate, insulin and/or a glutathione; and (b) at least one agent to be delivered to the CNS.

Gordon in U.S. Pat. No. 4,813,399 states that ferromagnetic particles that are under 1 μm in size can be injected into a patient. A steady magnetic or electric field may be used to enhance uptake of the particles by neuronal cells. Example IV describes a colloidal solution of $Fe_3O_4$-dextran-transferrin injected into a myelinated nerve.

Friedman et al. in WO 2015/038924 describes coating paramagnetic nanoparticles with a lipophilic drug and a polymer. The drug-bearing nanoparticles cross the BBB with the aid of a magnetic field. Although not described in detail, Friedman et al. suggest that the drug-bearing nanoparticles can be combined with chemotherapeutic agents.

Pell et al. in WO2013121359 describes a method for a temporary increase in a permeability of the blood brain barrier and administering a pharmaceutical substance to the brain, the method comprising: providing a system for transcranial magnetic stimulation in a range of at least 0.2 Hz; placing said system on a scalp; and providing a series of magnetic pulses to the brain via the system. Nanoparticles are not mentioned in this reference.

Numerous papers describe using a magnetic field to facilitate transport of drug-carrying superparamagnetic nanoparticles across the BBB. Nair et al. in US 20110213193, entitled Magnetic nanoparticle to transport API across brain blood barrier, use of magnetic field discuss the use of superparamagnetic nanoparticles to carry drugs through the BBB. Thomsen L B, Linemann T, Pondman K M, Lichota J, Kim K S, Pieters R J, Visser G M and Moos T., "Uptake and Transport of Superparamagnetic Iron Oxide Nanoparticles through Human Brain Capillary Endothelial Cells", ACS Chem Neurosci. 2013 Oct. 16; 4(10), pages 1352-1360 investigated the ability of fluorescent superparamagnetic iron oxide nanoparticles (SPIONs) to pass through human brain microvascular endothelial cells facilitated by an external magnet. The ability of SPIONs to penetrate the barrier was shown to be significantly stronger in the presence of an external magnetic force in an in vitro BBB model. The SPIONs can be coated with ligands or antibodies. Yan F, Wang Y, He S, Ku S, Gu W, Ye L., "Transferrin-conjugated, fluorescein-loaded magnetic nanoparticles for targeted delivery across the blood-brain barrier", J Mater Sci Mater Med. 2013 October; 24(10), pages 2371-2379 reported a strategy for brain targeted delivery utilizing the targeting of ligand conjugated nanoparticles to trigger the receptor-mediated transcytosis. In this study, transferrin (TO was employed as a brain targeting ligand to functionalize the fluorescein-loaded magnetic nanoparticles (FMNs). The Tf conjugated FMNs (Tf-FMNs) were characterized by transmission electron microscopy, thermal gravimetric analysis, Fourier transform infrared spectroscopy, and X-ray photoelectron spectroscopy. Using fluorescein as an optical probe, the potential of Tf-FMNs as brain targeting drug carriers was explored in vivo. It was demonstrated that Tf-FMNs were able to cross the intact BBB, diffuse into brain neurons, and distribute in the cytoplasm, dendrites, axons, and synapses of neurons. In contrast, magnetic nanoparticles without Tf conjugation did not cross the BBB efficiently under the same conditions. Fan C H, Ting C Y, Lin H J, Wang C H, Liu H L, Yen T C, Yeh C K., "SPIO-conjugated, doxorubicin-loaded microbubbles for concurrent MRI and focused-ultrasound enhanced brain-tumor drug delivery", Biomaterials 2013 May; 34(104), pages 3706-3715. DOX-SPIO-MBs ((doxorubicin; DOX), superparamagnetic iron oxide (SPIO), circulating microbubbles (MBs)) were designed to concurrently open the BBB and perform drug delivery upon FUS exposure, act as dual MRI and ultrasound contrast agent, and allow magnetic targeting (MT) to achieve enhanced drug delivery. The authors reported that DOX-SPIO-MBs were stable and provided significant superparamagnetic/acoustic properties for imaging. BBB-opening and drug delivery were achieved concurrently during the FUS exposure. Kong et al. in "Magnetic targeting of nanoparticles across the intact blood-brain barrier", Journal of Controlled Release 164 (2012) pages 49-57 "demonstrate in a mouse model that magnetic nanoparticles (MNPs) can cross the normal BBB when subjected to an external magnetic field . . . . Atomic force microscopy demonstrated that MNPs were internalized by endothelial cells, suggesting that trans-cellular trafficking may be a mechanism for the MNP crossing of the BBB."

Despite these references and other work, there remains a need for improved methods of transporting drugs across the BBB.

SUMMARY OF THE INVENTION

In a first aspect, the invention provides a method of administering a drug into the brain of a mammal (human or nonhuman), comprising: administering a MENP and a drug into the blood stream of a mammal; wherein the MENP attaches to the blood-brain barrier (BBB); applying a non-alternating (or slowly alternating so as to avoid localized heating (less than 40 kHz, preferably less than 10 kHz or less than 1 kHz or less than 50 Hz)) electric or magnetic field; and wherein the step of applying a non-alternating (or slowly alternating so as to avoid localized heating) electric or magnetic field causes an increase in the permeability of the BBB to the drug so that the drug passes into the brain while the MENP remains attached to the BBB.

It is not necessary that none of the MENP passes into the brain; however, preferably, the mass percent of (drug passing into brain/drug administered) is greater than the mass percent of (MENP passing into brain/MENP administered). Preferably less than 10 mass percent (or less than 5% or less than 1%) of the MENP passes into the brain.

In various embodiments, the method may further include one or more of the following: wherein the MENP is functionalized with a ligand for targeting receptors on the apical side of the endothelial cells that form part of the BBB; wherein the MENP attaches to the BBB via covalent bonding; wherein the MENP attaches to the BBB via noncovalent bonding; wherein the MENP comprises CoFe2O4/BaTiO3; wherein a static magnetic field is applied; and/or wherein the MENPs are loaded with drugs and, preferably, are capable of releasing the drug upon magnetic and/or electric stimulation.

One advantage of this approach is that since the functionalized MENPs are specifically targeted to the BBB-endothelium, the induced electric/magnetic fields is focused/localized at the BBB interface and therefore a much lower magnetic/electric stimulation level will be needed than what is typically used for tDCS or TMS. Other advantages may include: no additional chemicals such as mannitol are required; and heating of the BBB can be avoided.

Glossary

Drug—In the present invention, a drug is broadly defined as any substance that produces a therapeutic or psychological effect when it enters the brain.

Magneto-electric nanoparticles (MENPs) are a class of materials known as multiferroics i.e. materials that possess two or more ferroic orders—ferromagnetism and ferroelectricity. The MENPs have a non-zero magnetic moment and exhibit a strong magneto-electric coupling and can convert an externally-applied magnetic field into intrinsic electric dipole fields or voltage and vice versa. They can have a mass average size of between 10-200 nm (as determined by the longest dimension of each particle in a representative sample viewed by scanning electron microscopy (SEM)).

DESCRIPTION OF INVENTION

This invention relates to the development of a novel nanoparticle-neurostimulation platform to enable highly selective and reversible disruption of the BBB to temporarily increase its permeability for CNS drugs such as those intended for neurological diseases, brain tumor and nerve agent countermeasures. One advantage of our technology is that it can be independent of the type of drug (small molecule/large molecule, hydrophilic/hydrophobic/lipophilic) being delivered and can be readily applied to deliver any kind of drug. Another advantage is the minimal side effects of using this technology as it does not require the use of any chemicals (mannitol, verapamil, etc.) to disrupt the BBB. A third advantage is that the NPs to be used have high biocompatibility and the strength of magnetic/electric fields to be employed will be lower than that used for tDCS (transcranial direct current stimulation) or TMS (transcranial magnetic stimulation) used for BBB disruption (WO 2013/121359). In some embodiments of the invention a magnetic field of less than 1 T, or less than 0.5 T is applied, in some embodiments, a field in the range of 0.001 T to 0.1 T or 0.001 to 0.05 T is applied.

The NP platform described is composed of a relatively new class of nanomaterials called the magneto-electric nanoparticles (MENPs) (see, for example, WO201474584). These nanomaterials belong to a class of materials called multiferroics i.e., materials that possess two or more ferroic orders—ferromagnetism and ferroelectricity. These NPs have a non-zero magnetic moment like other magnetic NPs and can therefore respond to external magnetic fields.

However, unlike other magnetic NPs, they exhibit a strong magneto-electric coupling and can convert an externally-applied magnetic field into intrinsic electric dipole fields or voltage and vice versa. The invention preferably uses core/shell MENPs such as those made from $CoFe_2O_4$/$BaTiO_3$ (cobalt ferrite/barium titanate, sometimes written as $CoFe_2O_4@BaTiO_3$). However other core/shell type MENPs can also be used. The size of the MENPs can be between 10-200 nm. These nanoparticles can be spherical in shape or can be synthesized to be asymmetric such as rod-shaped or ellipsoidal.

Materials and techniques for synthesizing MENPs are known in the prior art. Some non-limiting examples of materials that have been mentioned in the literature (and are contemplated for use in this invention) for inclusion in MENPs include: iron oxide, superparamagnetic iron oxide, $BiFeO_3$, $BiCrO_3$, $TbMnO_3$, $BiMnO_3$, $YMnO_3$, $NiFe_2O_4$, $GaFeO_3$, $BiCrO_3$, $TbMnO_3$, $Bi_2FeCrO_6$, $BiMnO_3$, $HoMn_2O_5$, $YMn_2O_5$, $RMn_2O_5$ (R=Ho, Yb, Sc, Y, Ga, Dy, Er), $RMnO_3$ (R=Ho, Yb, Sc, Y, Ga, Dy, Er), $Fe_3O_4$, $Fe_2O_4$, $Fe_xPt_y$, $Co_xPt_y$, $MnFe_xO_y$, $CoFe_xO_y$, $NiFe_xO_y$, $CuFe_xO_y$, $ZnFe_xO_y$, and $CdFe_xO_y$, wherein x and y vary depending on the method of synthesis.

The MENPs can be functionalized with a ligand for targeting cell surface receptors on the apical (blood facing) side of the endothelial cells that form part of the BBB. These receptors include, but are not limited to, transferrin, insulin, melanotransferrin, LDL, leptin, thiamine and, glutathionine. Other targeting ligands such as the RVG peptide (for targeting the acetylcholine receptors), synthetic opioid peptides (such as Enkephalins), non-toxic analog of the diphteria toxin, CRM197 (for targeting the BBB endothelium receptor HB-EGF), and other cell penetrating peptides (such as TAT, RGD etc.) can also be used. The functionalized MENPs can be administered non-invasively through injection and will have the ability to "home" on to the BBB endothelium and bind to the endothelial cells. In another embodiment that MENPs can be guided to the brain through the use of DC magnetic field.

Once the MENPs bind to the BBB endothelium an external magnetic field can be applied through a pair of external magnetic coils. The magnetic field will induce a magneto-electric coupling in the MENPs which in turn will create an electric dipole field or electric potential (voltage) at the MENP-BBB interface. This electric field can disrupt the tight junction (TJ) proteins that form the paracellular barrier between the neighboring endothelial cells of the BBB. Once this barrier is disrupted, drugs can permeate to the brain side through the paracellular gap. It has been shown that an electric field of the order of 125-250 V/m is needed to cause TJ disruption in a monolayer cell model of bovine endothelial cells. The externally applied magnetic field of the order of 10-50 Oe can generate the required field.

The amount of the targeting ligand on the MENP surface will also be optimized so that the MENPs can either i) bind to the endothelial cells but are not internalized as proposed above or, ii) bind to the endothelial cells are internalized and delivered to the brain side through receptor mediated transcytosis. In another embodiment, the MENPs can itself transport to the brain side after BBB disruption. The MENPs can be functionalized to target specific cells (such as dopaminergic neurons) or neuromuscular junctions and can then be magnetically coupled to induce electric fields for stimulation of neurons or neural networks.

In another embodiment, once the MENPs bind to the BBB endothelium, an external electric field can be applied which will induce an electro-magnetic coupling in the particles resulting in the generation of a local magnetic dipole at the MENP-BBB interface which can also disrupt the TJ protein barrier.

In another embodiment the MENPs can be loaded with drugs and can be programmed to release the drug upon magnetic/electric stimulation. One way of doing this is to functionalize the MENPs with electrical/magnetic stimuli-responsive polymers and encapsulate the drug in these polymer coatings for an "on-demand" release. In this way, as soon as the BBB is disrupted (by the MENPs), the drug will be in its vicinity to diffuse to the brain side further increasing the efficacy of the drug delivery platform.

What is claimed:

1. A method of administering a drug into the brain of a mammal, comprising:
   administering a magneto-electric nanoparticle (MENP) and a drug into the blood stream of a mammal;
   wherein the MENP attaches to the blood-brain barrier (BBB);
   applying a non-alternating electric or magnetic field, or an electric or magnetic field alternating at less than 40 kHz so as to avoid localized heating; and
   wherein the step of applying an electric or magnetic field causes an increase in the permeability of the BBB to the drug so that the drug passes into the brain while the MENP remains attached to the BBB.

2. The method of claim 1 wherein the mass percent of drug passing into the brain relative to the mass of drug administered is greater than the mass percent of MENP passing into brain relative to the mass of MENP administered.

3. The method of claim 1 wherein less than 10 mass percent of the MENP passes into the brain.

4. The method of claim 1 wherein less than 1 mass percent of the MENP passes into the brain.

5. The method of claim 1 wherein the MENP is functionalized with a ligand for targeting receptors on the apical side of the endothelial cells that form part of the BBB.

6. The method of claim 1 wherein the MENP attaches to the BBB via covalent bonding.

7. The method of claim 1 wherein the MENP attaches to the BBB via noncovalent bonding.

8. The method of claim 7 wherein the MENPs are loaded with drugs and release the drug upon magnetic stimulation.

9. The method of claim 8 wherein the drug is encapsulated in a stimuli-responsive polymer.

10. The method of claim 1 wherein the MENP comprises $CoFe_2O_4/BaTiO_3$.

11. The method of claim 10 wherein the non-alternating magnetic field is applied and the non-alternating field is a static magnetic field.

12. The method of claim 1 wherein the MENPs are loaded with drugs and release the drug upon magnetic or electric stimulation.

13. The method of claim 1 wherein the alternating magnetic field is applied at a frequency of 50 Hz or less.

14. The method of claim 1 wherein, other than the MENP, no other chemicals are added to disrupt the BBB.

15. The method of claim 14 wherein less than 5 mass percent of the MENP passes into the brain.

16. A method of administering a drug into the brain of a mammal, comprising:
    administering a magneto-electric nanoparticle (MENP) and a drug into the blood stream of a mammal;
    wherein the MENP attaches to the blood-brain barrier (BBB);
    applying a non-alternating electric or magnetic field; and
    wherein the step of applying a non-alternating electric or magnetic field causes an increase in the permeability of the BBB to the drug so that the drug passes into the brain while the MENP remains attached to the BBB.

17. The method of claim 16 wherein the non-alternating electric or magnetic field is a static magnetic field.

18. A method of administering a drug into the brain of a mammal, comprising:
    administering a magneto-electric nanoparticle (MENP) and a drug into the blood stream of a mammal;
    wherein the MENP attaches to the blood-brain barrier (BBB);
    applying a non-alternating electric or magnetic field, or an alternating electric or magnetic field that avoids localized heating of the BBB; and
    wherein the step of applying an electric or magnetic field causes an increase in the permeability of the BBB to the drug so that the drug passes into the brain while the MENP remains attached to the BBB.

* * * * *